(12) United States Patent
Aarvak et al.

(10) Patent No.: US 9,119,807 B2
(45) Date of Patent: Sep. 1, 2015

(54) METHODS AND MATERIALS FOR THE GENERATION OF REGULATORY T CELLS

(71) Applicant: Life Technologies AS, Carlsbad, CA (US)

(72) Inventors: Tanja Aarvak, Oslo (NO); Anne-Marie Rasmussen, Oslo (NO); Gunnar Kvalheim, Oslo (NO); Walter Gabriell Borelli Piedras, Montevideo (UY); Anne Brunsvig, Stabekk (NO)

(73) Assignee: Life Technologies AS, Oslo (NO)

( * ) Notice: Subject to any disclaimer, the term of this patent is extended or adjusted under 35 U.S.C. 154(b) by 120 days.

(21) Appl. No.: 13/689,530

(22) Filed: Nov. 29, 2012

(65) Prior Publication Data

US 2013/0164312 A1 Jun. 27, 2013

Related U.S. Application Data

(63) Continuation of application No. 12/604,263, filed on Oct. 22, 2009, now abandoned, which is a continuation of application No. 12/279,713, filed as application No. PCT/IB2007/050508 on Feb. 15, 2007, now abandoned.

(30) Foreign Application Priority Data

Feb. 15, 2006 (GB) .................................. 603081.1

(51) Int. Cl.
*C12N 5/071* (2010.01)
*C12N 5/00* (2006.01)
*C12N 5/02* (2006.01)
*A61K 31/12* (2006.01)
*C12N 5/0783* (2010.01)

(52) U.S. Cl.
CPC .............. *A61K 31/12* (2013.01); *C12N 5/0636* (2013.01); *C12N 5/0637* (2013.01); *C12N 2501/999* (2013.01)

(58) Field of Classification Search
None
See application file for complete search history.

(56) References Cited

U.S. PATENT DOCUMENTS

| | | | |
|---|---|---|---|
| 4,336,173 | A | 6/1982 | Ugelstad |
| 4,459,378 | A | 7/1984 | Ugelstad |
| 4,654,267 | A | 3/1987 | Ugelstad et al. |
| 7,175,843 | B2 | 2/2007 | June et al. |
| 7,232,566 | B2 | 6/2007 | June et al. |
| 7,572,631 | B2 | 8/2009 | Berenson et al. |
| 7,977,095 | B2 | 7/2011 | Bonyhadi et al. |
| 2003/0157057 | A1 | 8/2003 | Horwitz |
| 2003/0228635 | A1 | 12/2003 | Hu et al. |
| 2008/0279826 | A1 | 11/2008 | Battaglia et al. |
| 2009/0148404 | A1 | 6/2009 | Berenson et al. |
| 2010/0068193 | A1 | 3/2010 | Brunsvig et al. |

FOREIGN PATENT DOCUMENTS

| | | |
|---|---|---|
| WO | WO-2004/050090 | 6/2004 |
| WO | WO-2005/003335 | 1/2005 |
| WO | WO-2007/110785 | 10/2007 |

OTHER PUBLICATIONS

Battaglia, et al., "Rapamycin Selectively Expands CD4+FCD25+FoxP3+Regulatory T Cells", *Blood*, vol. 105, No. 12, Jun. 15, 2005, 4743-4748.
Coenen, et al., "Rapamycin, and Not Cyclosporin A, Preserves the Highly Suppressive CD27+ Subset of Human CD4+CD25+ Regulatory T Cells", *Blood*, vol. 107, No. 3, Feb. 1, 2006, 1018-1023.
Dynal Dynabeads, "Product Information", 2007, 1-2.
Fu, et al., "TGF-Beta Induces Foxp3+T-Regulatory Cells From CD4+CD25-Precursors", *American Journal of Transplantation*, vol. 4, No. 10, Oct. 2004, 1614-1627.
Golovina, et al., "CD28 Costimulation Is Essential for Human T Regulatory Expansion and Function", *The Journal of Immunology*, vol. 181, No. 4, Aug. 15, 2008, 2855-2868.
Hoffmann, et al., "Large-Scale In Vitro Expansion of Polyclonal Human CD4+CD25high Regulatory T Cells", *Blood*, vol. 104, No. 3, Aug. 1, 2004, 895-903.
Invitrogen Dynal, "Dynabeads Human T-Expander CD3/CD28", 2009, 1-2.
Ito, et al., "OX40 ligand shuts down IL-10-producing regulatory T cells", *Proceedings of the National Academy of Sciences*, vol. 103, No. 35, Aug. 29, 2006, 13138-13143.
Keever-Taylor, C.A. et al., "Rapamycin added to human CD25+ cell cultures activated through CD3/CD28 enriches for CD4+CD25+CD27+Foxp3+ regulatory T cells", *Biology of Blood and Marrow Transplantation*, vol. 12, Issue 2, Supplemental 1, Feb. 2006, 14.
Komanduri, et al., "Graft-Versus-Host Disease After Allogeneic Stem Cell Transplantation: Evolving Concepts and Novel Therapies Including Photopheresis", *Biology of Blood and Marrow Transplantation : Journal of the American society for Blood and Marrow Transplantation*, vol. 12, No. 1, Suppl 2, Jan. 2006, 1-6.
Levine, et al., "Effects of CD28 Costimulation on Long-Term Proliferation of CD(+) T Cells in the Absence of Exogenous Feeder Cells", *Journal of Immunology*, vol. 159, Issue 12, Dec. 15, 1997, 5921-5930.
Li, et al., "CD3- and CD28-Dependent Induction of PDE7 Required for T Cell Activation", *Science*, vol. 283, Feb. 5, 1999, 848-851.
Loke, et al., "Emerging mechanisms of immune regulation: the extended B7 family and regulatory T cells", *Arthritis Research & Therapy*, vol. 6, No. 5, 2004, 208-214.
Luo, et al., "Anti-CD28 Antibody- and IL-4-Induced Human T Cell Proliferation Is Sensitive to Rapamycin", *Clinical & Experimental Immunology*, vol. 94, Issue 2, Nov. 1993, 371-376.
PCT/IB/050508, "International Search Report mailed Feb. 6, 2009", Oct. 4, 2007, 5 pgs.

(Continued)

*Primary Examiner* — Amy Juedes (57) ABSTRACT

Methods are disclosed for the generation of immunosuppressive regulatory T cells. The methods can include contacting a population of CD4+CD25− T cells with a T cell receptor (TCR)/CD3 activator, a TCR co-stimulator activator, and rapamycin. Kits for the generation of immunosuppressive regulatory T cells, methods of use, and cell populations are also disclosed.

6 Claims, 2 Drawing Sheets

(56) References Cited

OTHER PUBLICATIONS

Rutella, et al., "Regulatory T cells for immunotherapy of autoimmune diseases : From the bench to the beside", *Expert opinion on therapeutic patents 2005* United Kingdom, vol. 15, No. 11, 2005, 1595-1616.

Slavik, J. et al., "Rapamycin-resistant proliferation of CD8+ T cells correlates with p27kip1 down-regulation and bcl-xl induction, and is prevented by an inhibitor of phosphoinositide 3-kinase activity", *The Journal of Biological Chemistry*, vol. 279, No. 2, Jan. 9, 2004, 910-919.

Sommer, et al., "Signaling via CD28 costimulates lymphokine production, but does not reverse unresponsiveness to interleukin-2 in anti-CD3 triggered Th1 cells", *European Journal of Immunology*, vol. 23, No. 10, Oct. 2003, 2498-2502.

Sunder-Plassmann, et al., "Single T Human T Cells Stimulated in the Absence of Feeder Cells Transcribe Interleukin-2 and Under Long-Term Clonal Growth in Response to Defined Monoclonal Antibodies and Cytokine Stimulation", *Blood*, vol. 87, Issue 12, Jun. 15, 1996, 5179-5184.

Tian, et al., "Acceleration of Apoptosis in CD4+CD8 Thynocytes by Rapamycin Accompanied by Increased CD4+CD25+ T Cells in the Periphery", *Transplantation, Williams and Wilkins*, Baltimore, MD, US, vol. 77, No. 2, Jan. 27, 2004, 183-189.

Valmori, et al., "Rapamycin-Mediated Enrichment of T Cells with Regulatory Activity in Stimulated CD4+ T Cell Cultures is Not Due to the Selective Expansion of Naturally Occurring Regulatory T Cells but to the Introduction or Regulatory Functions in Conventional CD4+ T Cells", *The Journal of Immunology*, vol. 177, No. 2, Jul. 15, 2006, 944-999.

Wood, et al., "Regulatory T cells in Transplantation Tolerance", *Nature Reviews: Immunology*, vol. 3, Issue 3, Mar. 2003, 199-210.

METHODS AND MATERIALS FOR THE GENERATION OF REGULATORY T CELLS

CROSS REFERENCE TO RELATED APPLICATIONS

The present application is a continuation application of U.S. application Ser. No. 12/604,263, filed Oct. 22, 2009, which is a continuation application of U.S. application Ser. No. 12/279,713, filed Feb. 15, 2007, which is a 371 application of international application No. PCT/IB2007/050508, filed Feb. 15, 2007, which claims priority to G.B. patent application Serial No. 603081.1, filed Feb. 15, 2006, each of which are herein incorporated by reference in their entirety.

FIELD OF THE INVENTION

The invention relates to methods and materials for the generation of regulatory T cells.

SUMMARY OF THE INVENTION

The proliferation of T cells can be stimulated by contacting the cells with a T cell receptor/CD3 activator, a TCR co-stimulatory activator, and rapamycin. Methods for generating regulatory T cells from CD4+CD25+FOXP3− T cells and the use of these methods in the generation of T cell populations are disclosed. These cells can be used in a variety of applications including immunotherapy.

DESCRIPTION OF THE FIGURES

The following figures form part of the present specification and are included to further demonstrate certain aspects of the present invention. The invention may be better understood by reference to one or more of these figures in combination with the detailed description of specific embodiments presented herein.

DETAILED DESCRIPTION OF THE INVENTION

While compositions and methods are described in terms of "comprising" various components or steps (interpreted as meaning "including, but not limited to"), the compositions and methods can also "consist essentially of" or "consist of" the various components and steps, such terminology should be interpreted as defining essentially closed-member groups.

Aspects of the present invention relate to methods for generating CD4+CD25+FOXP3− regulatory T cells and the use of these methods in the generation of T cell populations which have applications in for example immunotherapy.

Naturally occurring regulatory T (Treg) cells suppress immune responses and play an important role in immunotherapy against autoimmune diseases and provide transplantation tolerance. Various populations of Treg cells have been described and include naturally occurring CD4+CD25+FOXP3+ cells and induced Tr1 and Th3 cells that secrete IL-10 and TGFβ respectively. The natural occurring CD4+CD25+FOXP3+ Treg cells represents 5-10% of the CD4+ T cells in the peripheral blood and are in a hypoproliferative state which has hampered detailed characterization and the potential use of these cells in immune therapy. In vivo uses therefore have relied on expansion protocols to generate sufficient numbers of Treg cells for in vivo use. The clinical use of Treg cells is limited by the lack of appropriate isolation and expansions protocols to generate sufficient numbers for in vivo infusion.

The present invention addresses this need by providing a method of generating a population of immunosuppressive Treg cells from the abundant CD4+CD25− T cell population. This provides Treg cells in sufficient numbers for in vivo infusions. The protocol can be used both for generating Treg cells for research purposes and for clinical use by infusion in patients.

The invention thus provides a method in which Treg cells expressing CD4, CD25 but not FOXP3 are generated. In one embodiment, the protocol uses a solid support carrying CD3/CD28 antibodies, Rapamycin and optionally cytokines, such as IL-4 and/or IL-2 to activate and expand CD4+ T cells isolated either from peripheral blood or leukopheresis products.

The use of anti-CD3/CD28, for example, provides the activation signal for the T cell population. T cells require at least two signals for activation. Signal one is antigen specific and is elicited by peptide/major histocompatibility complex (MHC) complexes presented by antigen-presenting cells (APC) and received through the T-cell receptor (TCR)/CD3 complex. Signal two (which is antigen non-specific) is also delivered by antigen presenting cells and one of the candidate molecules for its receptor is the T cell antigen CD28. It is thought that when both the TCR/CD3 and CD28 T cell receptors are occupied by appropriate ligands, T cells are stimulated to proliferate and produce IL-2 (a cytokine essential for T cell proliferation), whereas occupation of the T cell receptor alone favors T cell anergy or apoptosis.

In vitro it has been shown that T cell growth and cytokine production can be stimulated by culturing T cells with anti-CD3 antibodies which have been immobilized to a solid phase (for example beads or tissue culture plates) and adding soluble CD28 antibodies (Sommer et al., 1993. *Eur. J. Immunol.* 23:2498-2502, Sunder-Plassmann et al., 1996. *Blood* 87:5179-5184). More recently it has been shown that co-immobilising both CD3 and CD28 antibodies to the same solid phase or to different solid phases can also induce T cell proliferation (Levine et al., 1997. *J. of Immunol.* 159: 5921-30; Li et al., 1999. *Science* 283:848-851).

Rapamycin is an immunosuppressive agent used to prevent allograft rejection. Recently, the cellular target for Rapamycin in vitro has been discovered, and shown to selectively expand naturally occurring CD4+CD25+FOXP3+ regulatory T cells. The present inventors have developed a new protocol using Rapamycin to generate new Treg cells from CD4+CD25− T cells. In contrast to naturally occurring CD4+CD25+ Treg cells that express FOXP3, the Treg cells generated in accordance with the invention do not express FOXP3 but still show very strong suppressive capacities.

Treg cells generated according to the invention have many potential uses, including experimental and therapeutic uses. In particular it is envisaged that such T cell populations will be extremely useful in suppressing undesirable or inappropriate immune responses. In such methods a small number of T cells are removed from a patient and then manipulated and expanded ex vivo before reinfusing them into the patient. Examples of diseases which may be treated in this way are autoimmune diseases and conditions in which suppressed immune activity is desirable, e.g. for allo-transplantation tolerance. A therapeutic method could comprise providing a mammal, obtaining CD4+CD25− T cells from the mammal; expanding/activating the T cells ex vivo in accordance with the methods of the invention as described above; and administering the expanded/activated T cells to the mammal to be treated. The first mammal and the mammal to be treated can be the same or different. The mammal can generally be any mammal, such as cats, dogs, rabbits, horses, pigs, cows, goats, sheep, monkeys, or humans. The first mammal ("donor") can be syngeneic, allogeneic, or xenogeneic. Therapy could be administered to mammals having aberrant immune response (such as autoimmune diseases including, for example diabetes, multiple sclerosis, myasthenia gravia, neuritis, lupus, rheumatoid arthritis, psoriasis, and inflammatory bowel disease), tissue transplantation, or fertility treatments.

The main technical hurdles involved in such therapies include the purification of the cells of interest from the patient and the expansion and/or the manipulation of the cells in vitro. Such therapies generally require a large number of cells and thus it can be seen that it is vital to optimize the methods of inducing in vitro T cell proliferation in order to maximize the number of T cells produced and minimize the time required to produce the T cells in sufficient numbers.

Thus viewed in a first aspect the present invention provides a method for stimulating proliferation of CD4+CD25− T cells comprising contacting the cells with a T cell receptor (TCR)/CD3 activator, a TCR co-stimulator activator and rapamycin. The cells can be cultured under conditions and for a time suitable to achieve levels of proliferation as described hereinafter. This method generates a CD4+CD25+ T cell population. T cells which are FOXP3− may be used and the generated T cell population in that case remain FOXP3−.

An alternative embodiment of the invention provides a method of preparing a T cell population of CD4+CD25+ T cells, preferably CD4+CD25+FOXP3− T cells, comprising contacting CD4+CD25− T cells (preferably CD4+CD25−FOXP3− cells) with a TCR/CD3 activator, a TCR co-stimulatory activator and rapamycin to stimulate proliferation of the CD4+CD25− T cells and optionally isolating the T cell population. The CD4+CD25+ (preferably CD4+CD25+FOXP3−) T cell population thus formed provides a further aspect of the invention. Preferably, the T cell population thus formed is immunosuppressive. Thus, the cells are able to suppress proliferation of syngeneic T cells in vitro, e.g. as described in the Examples herein. At a 1:1 ratio of the test T cells, with, for example, T cells prior to stimulation, immunosuppressive cells preferably achieve at least 70, 80 or 90% suppression of proliferation, i.e. reduction in cell numbers relative to control over a suitable culture period, e.g. between 2 and 14 days, for example 4 days. Preferably, the CD4+CD25− T cells used in the stimulation methods and the CD4+CD25+ T cells generated according to the invention as described herein are FOXP3

The TCR/CD3 activator can be an antibody or ligand for TCR/CD3, for example a CD3 antibody. The TCR co-stimulatory activator can be an antibody or ligand for CD28, CD137 (4-1BB), GITR, B7-1/2, CD5, ICOS, OX40 or CD40. Preferably the TCR/CD3 activator is a CD3 antibody and the TCR co-stimulatory activator is a CD28 antibody.

Preferably the activators, e.g. antibodies, are immobilized to a solid phase. The activators, e.g. antibodies may be provided at variable concentration on the solid support, such as at a ratio of about 1:10 to about 10:1 of CD28 antibody to TCR/CD3 antibody. Optionally more than one of the TCR/CD3 activators and/or more than one of the TCR co-stimulatory activators may be used in methods of the invention.

"Stimulating proliferation" as used herein refers to any event which results in a detectable increase or expansion in the number of T cells present when compared with the number present in the absence of such stimulation. The daughter cells which are generated by the proliferation may have a different phenotype as a result of stimulation, in particular, stimulation results in CD25 expression thus resulting in the generation of CD4+CD25+ cells from CD4+CD25− cells.

Such an increase in number may be relatively small, but is preferably a significant increase such as for example an increase in cell number of at least about 2 fold, preferably at least about 5 fold, about 20 fold or about 50 fold and more preferably at least about 100 fold, about 500 fold, or greater than about 1000 fold. Such increases in number may be measured at any appropriate time point in the cell expansion protocol, such as for example at day 4 up to day 12 of the cell expansion protocol.

T cells which are considered positive for a specific antigen, e.g. CD3, carry detectable levels of the antigen, e.g. as determined by cell sorting (e.g. flow cytometry) or the use of a solid support to which an appropriate binding partner, e.g. antibody is bound.

As discussed above stimulation of T cells with a TCR/CD3 activator and a TCR co-stimulatory activator, e.g. anti-CD3 and anti-CD28 antibodies also provides the two signals required for T cell activation. Thus, viewed in a yet further alternative way, the present invention provides a method of activating CD4+CD25− T cells comprising contacting the cells with a TCR/CD3 activator and a TCR co-stimulatory activator (e.g. CD28 antibodies and T cell receptor (TCR)/CD3 antibodies) and rapamycin.

Thus, throughout the discussion of the present invention, reference to methods of stimulating proliferation and use of T cells so stimulated should also be read to include methods of stimulating T cell activation and the use of such activated T cells.

Any CD4+CD25− T cell population may be expanded/activated using the present method. For example the T cell population may comprise CD4+CD25−CD8+ T cells. In a preferred aspect, CD4+CD25− T cells are separated from the source starting material prior to stimulation and expansion. Thus, in a preferred aspect the present invention provides a method for stimulating proliferation of CD4+CD25− T cells comprising at least the steps of: (i) isolating CD4+CD25− T cells from a sample, and (ii) contacting the cells with a TCR/CD3 activator and a TCR co-stimulatory activator (e.g. CD28 antibodies and T cell receptor (TCR)/CD3 antibodies) and rapamycin.

An additional embodiment of the invention provides a method of preparing a T cell population of CD4+CD25+ (preferably CD4+CD25+FOXP3−) T cells, comprising (i) isolating CD4+CD25− T cells from a sample, and (ii) contacting the cells with a TCR/CD3 activator and a TCR costimulatory activator (e.g. CD28 antibodies and T cell receptor (TCR)/CD3 antibodies) and rapamycin to stimulate proliferation of the CD4+CD25− T cells and optionally isolating the T cell population.

The CD4+CD25− cells which are used in methods of the invention may comprise the entire CD4+CD25− T cell population or a portion of that population. For example, a sub-population may be used in the method, e.g. CD4+CD25−FOXP3−, which sub-population may be used in its entirety or a portion of that sub-population may be used. Thus the isolated CD4+CD25− cells subjected to the stimulation method of the invention may contain at least about 20%, about 30%, about 40%, about 50%, about 60%, about 70%, about 80%, or about 90% of the CD4+CD25− cells (or a sub-population thereof) in the sample from which the CD4+CD25− cells were isolated. Preferably however, in order to generate sufficient levels of Treg for in vivo uses, essentially the entire CD4+CD25− population from the starting sample is used in methods of the invention.

The stimulation method may be performed in the presence of other cells, e.g. other T cells, such as CD4+CD25+ cells which themselves will proliferate during the method of the invention. Thus in the above described protocol, the step of isolating CD4+CD25− T cells may comprise isolating a significant portion (i.e. at least 20, 30, 40, 50, 60, 70, 80 or 90%) or all CD4+ cells, i.e. which include both CD25− and CD25+, from the sample. Thus in a preferred embodiment of the invention, the isolation step comprises the isolation of CD4+ cells. Furthermore, other cells may also be present such that the e.g. CD4+, CD4+CD25− and/or CD4+CD25−FOXP3− cells form only a portion of the cells used in the stimulatory method, before or after the isolation step. Thus in the stimulatory step the CD4+CD25− may be present as a portion of the cells subject to stimulation, i.e. an enriched preparation may be used, such as comprising at least about 50, about 60, about 70, about 80 or about 90% of the total cells subjected to stimulation.

Preferably however, at least some CD4+CD25+ cells are absent, e.g. at least about 10%, about 20%, about 30%, about 40%, about 50%, about 60%, about 70%, about 80%, or about 90% of the cells which appeared in the starting material are absent. Alternatively expressed the cells for stimulation/expansion are preferably substantially all CD4+CD25− cells, such as at least about 80%, about 90%, about 95% or about 98% CD4+CD25− T cells are used in the method. Especially preferably, at least some CD4+FOXP3+ cells are absent in the cells used for expansion, e.g. at least 10, 20, 30, 40, 50, 60, 70, 80 or 90% of the cells which appeared in the starting material of the sample are absent. Alternatively expressed the cells for stimulation/expansion are preferably substantially all CD4+ FOXP3− (preferably CD4+CD25−FOXP3−) T cells, e.g. at least 80, 90, 95 or 98% CD4+FOXP3− or CD4+CD25− FOXP3− T cells are used in the method.

Sources of T cells and methods of isolating particular T cell populations (e.g. CD4+ cells) which can be expanded by stimulation according to the methods of the present invention are well known and described in the literature. Thus for example T cells may conveniently be isolated from the blood e.g. from a peripheral blood mononuclear cell (PBMC) population isolated from blood, or from other blood-derived preparations such as leukopheresis products or from bone marrow, lymph, thymus, spleen or umbilical cord. Examples of T cell populations which can be selected and expanded according to the methods of the present invention include those which are derived by negative selection from PBMC where B cells and monocytes are depleted, (optionally negative selection of CD25− and/or FOXP3− cells), positive selection of the CD4+ T cells using beads coupled with Abs against CD4 (or flow cytometry) and positive selection of T cells using sheep red blood cells. T cell populations may be derived from any appropriate source, including human or animal sources.

Immobilization of the activators (e.g. CD28 and CD3/TCR antibodies) to a solid phase according to the present invention means that the activators are immobilized to (or on) the same or different solid supports. Preferably, the antibodies are co-immobilized to (or on) the same surface.

"Immobilized" or "Immobilization" as used herein refers to any means by which activators, e.g. antibodies can be bound, attached or otherwise fixed to a solid phase. Such immobilization may be direct (i.e. the activators themselves are attached to the solid phase) or indirect (i.e. the activators are attached via an intermediate entity) and may occur by way of any chemical or non-chemical attachment method. Such methods include immobilization of activators by adsorption and/or by covalent attachment or via affinity between molecules (e.g. immobilization on an avidin-coated surface of biotinylated antibodies, or the immobilization of an anti CD3 or anti CD28 via a secondary antibody or antibodies which are themselves attached to the solid phase). The immobilization must be of sufficient strength that the activators are not removed under the conditions used to prepare the solid phase with the activators attached (for example the immobilized activators must withstand the washing conditions etc. associated with the preparation of the solid phase) and are also not removed under the conditions used to stimulate T cell proliferation.

The step of "contacting" the population of T cells with the activators, e.g. immobilized to the solid phase, may be carried out in any convenient or desired way. When the method is performed without immobilized activators, the activators are added into the solution containing the cells to be expanded. When one or more of the activators is carried on a solid support, e.g. if the solid phase was a tissue culture plate or flask or some other flat surface, the population of T cells, conveniently in an aqueous medium such as for example an appropriate cell culture medium, may simply be added to the solid phase under appropriate conditions. Alternatively, if the solid phase is particulate (for example beads) the solid phase itself may be added to the T cell population under appropriate conditions. In any event, in the contacting step, the cells are contacted with activators which are already immobilized i.e. the activators are bound to the solid support before they bind to the cells, i.e. before the contacting step.

The activators are provided in a molar equivalent or molar excess to the cells to be stimulated. Thus, for example in the case of anti-CD3/anti-CD28 solid supports, e.g. beads, the bead to T cell ratio may range from 1:10 to 1:1, e.g. 3:1. Beads for this purposes are well known in the art (e.g. from Dynal Biotech ASA).

Appropriate conditions will be such conditions which are suitable for T cell growth and should be chosen depending on for example the T cell population concerned and the particular cell culture medium used. Such media and conditions are well known in the art. Typical conditions may be maintenance of cells in a humidified atmosphere containing 5 or 10% $CO_2$ at 37° C. or under low $O_2$ concentration (e.g. 2%). Appropriate culture medium is selected depending on the T cell population being expanded. For example for T cell populations the culture medium X vivo 15 supplemented with 5% human AB serum is appropriate or RPMI 1640 with FCS, CellGro DC, or or other media suited for cell culture may be used.

Rapamycin is contacted with the cells prior to, simultaneously with, and/or subsequent to contact of the cells with the activators. Rapamycin is preferably present throughout the proliferation/expansion step in the method according to the invention. The rapamycin may be added in one or more steps. Thus for example, as described in the examples herein, isolated CD4+ cells may be stimulated with activators (CD3 antibodies and CD28 antibodies) and rapamycin at the same time. In this method, subsequent growth and passaging is performed in the presence of rapamycin, but not the activators.

Rapamycin may be used at a concentration of from about 0.01 µM to about 10 µM, such as about 0.5 µM to about 2 µM, or about 1 µM. Rapamycin is a protein kinase inhibitor with a molecular weight of 914.2, also referred to as Sirolimus, Rapamune, AY-22989, RAPA and NSC-226080, available from Sigma, Calbio Chem, LC Labs etc. Rapamycin is available from a variety of commercial sources, such as A.G. Scientific, Inc. (San Diego, Calif., USA).

Other cytokines and/or growth factors may be added to the cultures as appropriate. Such cytokines and/or growth factors are added at appropriate concentrations and time points. For example IL-2 and/or IL-4 may be added to enhance the proliferation of the T cells and other cytokines may be added to induce particular differentiation patterns if required (e.g. TGF-β and IL10). For example IL-4 has been shown to trigger differentiation of T cell populations into the Th2 subpopulation and IFN– to trigger differentiation into the Th1 subpopulation (Sunder-Plassmann, supra). Thus in preferred embodiments of the invention, a cytokine, e.g. IL-2 is preferably added, e.g. at a final concentration of 10-2,000 U/ml, e.g. at 20 U/ml during stimulation and at 1,000 U/ml periodically during the initial culture period and 20 U/ml in the period prior to harvest. IL-4 is preferably added, e.g. at a final concentration of 1,000-5,000 U/ml, e.g. at 1,000 U/ml during stimulation periodically during the initial culture period and in the period prior to harvest. Appropriate cytokines and growth factors and their effects on T cells are well known and described in the art. Once the T cell population has been brought into contact with the activators and rapamycin under appropriate conditions for growth of the T cells, growth is allowed to progress for a time period selected according to the final number of T cells required and the rate of expansion of the cells. Passaging of the cells may be undertaken during this period. Such a time period is normally between 3 and 10 days but can be as long as 14 to 20 days or even longer providing the viability and continued proliferation of the T cells is maintained.

If necessary the T cell population which is being expanded/activated according to the methods of the present invention may be re-stimulated by contacting the cells with further activators in a similar way to the initial stimulation. In general, re-stimulation is only necessary or desired if the T cells are to be cultured for a long period of time, e.g. more than 20 days.

Treg cells having immunosuppressive properties can be assessed by analysis of their phenotype (CD4+CD25+ FOXP3–) and their ability to suppress proliferation of syngeneic T cells in vitro, e.g. as described in the Examples herein.

Once a T cell population has been expanded to a required level as described above, the expanded population can then be separated from the solid phase in an appropriate way. For example, if the activators are attached to a solid phase and that solid phase is a tissue culture well, plate or bottle, the T cell population can be obtained by removal of the culture medium which contains the T cells. If the solid phase comprises for example magnetic beads, a magnetic field is used to attract the beads to the side of the vessel and the culture medium containing the T cells can then be poured off. Other particulate solid supports e.g. non-magnetic beads may be centrifuged or filtered away from the cells. Although the majority of T cells will be located in the culture medium, some T cells are likely to be attached to the solid phase after expansion. If desired such T cells can be detached by for example resuspension using a pipette or other suitable means. Such a resuspension will normally be carried out before the T cells are separated from the solid phase to improve the yield. Once separated from the solid phase the T cell population can then be further treated and/or manipulated in any desired way or used directly for suitable applications such as for example in vitro experiments and research, non-therapeutic applications, therapeutic applications etc. as discussed below.

When soluble activators are employed, these may be removed by competition with appropriate ligands, e.g. CD3 or CD28, but more preferably the T cells are collected from the culture medium and used for applications as described herein without further refinement. Conveniently, for large scale applications, appropriate isolation and preparation platforms may be used for selection of the T cell populations for stimulation and/or for the expansion protocol and/or isolation of the generated T cell population. In this regard special mention may be made of Dynal's ClinExVivo™ platforms in which closed sterile disposable bags may be used for any magnetic cell separation steps which are performed, e.g. for cell isolation prior to, or after, expansion.

Thus in a preferred aspect the present invention provides a method for stimulating proliferation of CD4+CD25– T cells comprising at least the steps of: (i) isolating CD4+CD25– T cells from a sample, preferably by a method comprising at least the steps of contacting the sample with a solid support carrying CD4 antibodies and isolating the T cells which bind to the solid support, or using negative isolation of CD4+ T cells by removing all unwanted cells with a mix of mAbs followed by magnetic beads to capture cells (ii) contacting the cells with a) a solid support carrying CD28 antibodies and TCR/CD3 antibodies and b) rapamycin, (iii) incubating the cells under conditions to allow proliferation, preferably in the presence of IL-4 and/or IL-2 and (iv) isolating the T cells after the incubation.

When the activator used in accordance with the invention is an antibody reactive with TCR co-stimulatory activators: CD28, CD137 (4-1 BB), GITR, B7-1/2,C D5, ICOS, OX40, CD40 or CD137 or TCR/CD3 activators: CD3 or TCR may be used. More than one antibody from each group may be used. Preferably a TCR or CD3 antibody is used in conjunction with a CD28 antibody. Thus, using CD28 and TCR/CD3 antibodies as an example, a "CD28 antibody" and a "TCR/CD3 antibody" according to the present invention are antibodies capable of binding to (or immunoreactive with) CD28 or TCR/CD3 respectively. Preferred are antibodies capable of binding specifically to CD28 or TCR/CD3 in a manner which distinguishes from the binding to other "non-target" molecules, i.e. preferred antibodies are those which exhibit detectable binding affinity for CD28 or CD3/TCR but whose binding to other molecules, for example other cell surface molecules is negligible, insignificant or non-detectable. In preferred aspects of the invention, the method of the invention may involve the use of antibodies to (i) CD3 and CD28, (ii) CD3 and CD137, or (iii) CD3 and CD28 and CD137.

A number of CD28, CD137 (4-1BB), GITR, B7-1/2, CD5, ICOS, OX40, CD40, CD3 or TCR antibodies (or anti-CD28 etc.) are known in the literature or commercially available. Any such antibody, or its fragments or derivatives may be used (so long as they retain binding activity).

Antibodies for use in methods of the present invention may be of any species, class or subtype providing that such antibodies can react with the target of interest, e.g. CD3, the TCR, or CD28 as appropriate.

Thus "antibodies" for use in the present invention include:
(a) any of the various classes or sub-classes of immunoglobulin, e.g. IgG, IgA, IgM, IgD or IgE derived from any animal e.g. any of the animals conventionally used, e.g. sheep, rabbits, goats, or mice, or egg yolk (b) monoclonal or polyclonal antibodies (c) intact antibodies or fragments of antibodies, monoclonal or polyclonal, the fragments being those which contain the binding region of the antibody, e.g. fragments devoid of the Fc portion (e.g. Fab, Fab', F(ab')2, scFv), the so called "half molecule" fragments obtained by reductive cleavage of the disulphide bonds connecting the heavy chain components in the intact antibody. Fv may be defined as a fragment containing the variable region of the light chain and the variable region of the heavy chain expressed as two chains.

(d) antibodies produced or modified by recombinant DNA or other synthetic techniques, including monoclonal antibodies, fragments of antibodies, "humanised antibodies", chimeric antibodies, or synthetically made or altered antibody-like structures. Also included are functional derivatives or "equivalents" of antibodies e.g. single chain antibodies, CDR-grafted antibodies etc. A single chain antibody (SCA) may be defined as a genetically engineered molecule containing the variable region of the light chain, the variable region of the heavy chain, linked by a suitable polypeptide linker as a fused single chain molecule.

Methods of preparation of antibody fragments and synthetic and derivatized antibodies are well known in the art and widely described in the literature and will not be described herein.

In a preferred embodiment of the invention CD3 and CD28 antibodies are used and more preferably these antibodies are monoclonal antibodies. Preferred CD28 antibodies are L293 (Becton Dickinson), Mab 9.3 (an IgG2A antibody, Dr. Ledbetter, Bristol Myers Squibb Corporation, Seattle, Wash.), Mab Kolt-2 (IgG1), 15E8 (IgG1), 248.23.2 (IgM), YTH913.12 (Monosan), CD28.2 (Coulter), EX5.3D10 (IgG2A), and B-T3 clone (Diaclone, France). Preferred CD3 antibodies are Spv.T3b, OKT-3 (Ortho Pharmaceutical), MEM-57 and WT32 (Monosan), SK7 (Becton Dickinson), UCHTI (Coulter), HIT3a (Pharmigan), and clone BC3 (Fred Hutchinson Cancer Research Centre, Seattle). Preferred TCR antibodies are the clone BL-A (Monosan).

Solid phases for use in the present invention may be any solid surfaces to which activators, e.g. antibodies or antibody fragments can be immobilized either directly (i.e. the antibodies themselves are attached to the solid phase) or indirectly (i.e. the antibodies are attached via an intermediate entity, for example a secondary antibody, which is itself attached to the solid phase). For example, such solid phases may comprise glass, silica, latex, polymeric materials, plastic, tissue culture plastic, dextran, cellulose and PEG, iron and other metals. Such solid supports may take the form of any of the well known supports or matrices which are currently used for immobilization or separation, for example particles, beads, bottles, tubes, strips plates or wells, sheets, fibres, capillaries, needles, combs, pipette tips, microarrays, chips, filters, membranes, and so on.

Preferably the solid phase is a particulate material. Conveniently, a particulate solid support used according to the invention will comprise spherical beads. The size of the beads or indeed any other particulate form of support is not critical, but they may for example be of the order of diameter of at least 1 and preferably at least 2 µm, and have a maximum diameter of preferably not more than 10 µm and more preferably not more than 6 µm. For example, preferred beads for use in the present methods have a diameter of 4.5 µm though smaller particles such as those with a diameter of 1 µm or 2.8 µm may be used. Small particles, for example beads of diameter less than 1 µm, may be cross-linked to provide larger complexes.

Monodisperse particles, that is those which are substantially uniform in size (e.g. size having a diameter standard deviation of less than 5%) have the advantage that they provide very uniform reproducibility of reaction. Monodisperse polymer particles produced by the technique described in U.S. Pat. No. 4,336,173 are especially suitable.

Non-magnetic polymer beads suitable for use in the method of the invention are available from Dynal Biotech ASA (Oslo, Norway) as well as from Qiagen, Amersham Pharmacia Biotech, Serotec, Seradyne, Merck, Nippon Paint, Chemagen, Promega, Prolabo, Polysciences, Agowa and Bangs Laboratories.

However, to aid manipulation and separation, magnetic or magnetizable beads are preferred. The term "magnetic" as used herein means that the support is capable of having a magnetic moment imparted to it when placed in a magnetic field, and thus is displaceable under the action of that field. In other words, a support comprising magnetic particles may readily be removed by magnetic aggregation, which provides a quick, simple and efficient way of separating the particles, and is a far less rigorous method than traditional techniques such as centrifugation which generate shear forces which may disrupt cells.

Thus, the magnetic particles may be removed onto a suitable surface by application of a magnetic field e.g. using a permanent magnet. It is usually sufficient to apply a magnet to the side of the vessel containing the sample mixture to aggregate the particles to the wall of the vessel.

Especially preferred particles are superparamagnetic particles as magnetic aggregation and clumping of the particles during reaction can be avoided. Such particles are described, for example, by Sintef in EP-A-106873. The well-known magnetic particles sold by Dynal Biotech ASA (Oslo, Norway) under the trade mark DYNABEADS®, are particularly suited for use in the present invention. Particularly preferred beads for use in the present invention are Dynabeads M-450.

Functionalized coated particles for use in the present invention may be prepared by modification of the beads according to U.S. Pat. Nos. 4,336,173, 4,459,378 and 4,654,267 or by other procedures known in the art. Thus, beads, or other supports, may be prepared having different types of functionalized surface, for example positively or negatively charged, hydrophilic or hydrophobic. Hydrophobic surfaces (for example hydrophobic resins) are particularly preferred for use in the attachment of antibodies, as, by way of a hydrophobic interaction, the antibodies will be adsorbed to the surface of the beads. This adsorption is optionally followed by chemical linkage, for example covalent linkage of the antibodies to the surface of the beads. Methods for forming such chemical or other linkages are well known and documented in the art.

Based on the varying physical and/or chemical properties of the activators, e.g. antibodies used, such as hydrophobicity and isoelectric point, binding profiles will vary slightly for different activators. This is dealt with by adapting the reaction conditions in order to obtain the required levels of activators, e.g. by modifying the ratio of activators immobilized on the solid surface, when a solid support is used. An indication of the ratios of activators which become bound to a solid phase under certain reaction conditions can be assessed by a person skilled in the art for example by immobilizing anti-CD3 and anti-CD28 antibodies of different sub-classes onto the solid phase under certain conditions and then using individual reagents which react specifically with antibodies of the particular sub-classes in question to determine in turn the amount and hence the ratio of the different antibodies bound.

Magnetic or magnetizable beads are particularly preferred because of the ease of manipulation. In addition, as described above, preferably the beads have a hydrophobic surface. Thus, to prepare beads for use in the methods of the present invention the magnetic and hydrophobic beads are incubated with an appropriate mixture of the activators, e.g. CD3/(or TCR) and CD28 antibodies under appropriate reaction conditions to facilitate adsorption and optionally chemical linkage of activators to the surface of the beads.

The activators, in appropriate ratios, are generally mixed together before they are put into contact with the beads. "Appropriate reaction conditions" as discussed above will vary according to the particular activators used but exemplary conditions may comprise for example an incubation of the beads and activators, e.g. antibodies in a phosphate buffer (for example 0.5 M phosphate) of pH 7.4 and a particle concentration of $4 \times 10^8$ beads/ml. Human serum albumin or other serum albumin such as bovine serum albumin may optionally be present (e.g. at a concentration of about 0.05% w/v) to stabilize the activators and block any remaining hydrophobic patches on the surface of the beads.

Once the appropriate reaction mixture has been set up the reaction is allowed to progress for an appropriate time and under appropriate conditions to facilitate the activator absorption to the surface in the required ratio. Again the particular conditions can be varied depending on the components of the reaction mixture but exemplary conditions include incubation for 16-24 hours at 37° C. with slow tilt and rotation.

Whatever the conditions chosen, once the immobilization reaction is complete the beads with activators immobilized to their surfaces in the appropriate ratio can be removed from the remaining aqueous medium by placing a magnet at the side of the reaction vessel and discarding the supernatant. The beads will generally be washed to remove any excess non bound antibodies and are then ready for use. Such beads, once prepared, can be used immediately or can be stored for future use.

A yet further aspect of the invention provides the use of the methods of the invention in the expansion/activation of T cell populations for use in in vitro experiments and research. A yet further aspect of the invention provides the use of the methods of the invention in the expansion/activation of T cell populations for the generation of T cell populations for immune suppression therapy. In such a therapy a T cell sample is taken from a patient and manipulated ex vivo as described hereinbefore to isolate and expand an appropriate T cell population before reinfusing the T cell population to a patient to suppress the patient's immune response.

Thus, a yet further aspect of the invention provides a method of treatment of a mammal with a condition or disease typified by an aberrant immune response or in which immune suppression would be advantageous, comprising administering to the mammal T cells prepared in accordance with the method of the invention. Thus in a particular embodiment, the method comprises:

a) obtaining CD4+CD25− T cells from a first mammal;
b) expanding/activating the T cells ex vivo in accordance with the methods of the invention as described above; and
c) administering the expanded/activated T cells to the mammal to be treated.

This method thus provides a method of achieving an immunosuppressive effect in a mammal, i.e. a method of preventing an immune response. An effective amount of the T cells is administered to achieve the desired therapeutic effect, e.g. by intravenous injection in a pharmaceutically acceptable diluent.

The mammal to be treated may be the same as the first mammal from which the T cells are sourced or may be a different mammal, i.e. a recipient of T cells from a donor. When a donor is used, the donor is preferably syngeneic, but may also be allogeneic or even xenogeneic provided the cells are subject compatible.

The condition or disease typified by an aberrant immune response may be an autoimmune disease, for example diabetes, multiple sclerosis, myasthenia gravia, neuritis, lupus, rheumatoid arthritis, psoriasis or inflammatory bowel disease. Conditions in which immune suppression would be advantageous include conditions in which a normal or an activated immune response is disadvantageous to the mammal, e.g. allo-transplantation of e.g. body fluids or parts, to avoid rejection, or in fertility treatments in which inappropriate immune responses have been implicated in failure to conceive and miscarriage. The use of such cells before, during, or after transplantation avoids extensive chronic graft versus host disease which may occur in patients being treated (e.g. cancer patients). The cells may be expanded immediately after harvest or stored (e.g. by freezing) prior to expansion or after expansion and prior to their therapeutic use. The therapies may be conducted in conjunction with known immunosuppressive therapies.

As used herein, "treating" refers to the reduction, alleviation or elimination, preferably to normal levels, of one or more of the symptoms of the disease or condition which is being treated, e.g. alleviation of immune dysfunction or avoidance of transplant rejection, relative to the symptoms prior to treatment.

Preferably the mammal is a domestic or livestock animal (e.g. cats, dogs, rabbits or horses, pigs, cows, goats, sheep) or a primate, e.g. a human.

Alternatively viewed, this aspect of the invention also provides the use of a T cell population obtained by the stimulation method of the present invention in the preparation of a therapeutic composition for achieving an immunosuppressive effect in a mammal, e.g. for treating a mammal with a condition or disease typified by an aberrant immune response or in which immune suppression would be advantageous.

Alternatively, aspects of the invention provide the use of a TCR/CD3 activator, a TCR co-stimulatory activator, and/or rapamycin in the preparation of a medicament comprising a T cell population obtained by the stimulation method of the present invention for achieving an immunosuppressive effect in a mammal, e.g. for treating a mammal with a condition or disease typified by an aberrant immune response or in which immune suppression would be advantageous.

Methods of obtaining a T cell sample from a patient (or an animal source if appropriate) and isolating CD4+ cells for expansion/activation are well known and documented in the art. For example, peripheral blood mononuclear cells can be obtained from buffy coats of normal blood donors by density gradient centrifugation and leukopheresis. Adherent mononuclear cells can then be separated from non-adherent mononuclear cells by adherence to a solid surface such as for example beads or tissue culture plastic under appropriate conditions (e.g. 30 minutes to 2 hours at 37° C.). Enriched T cells can be used directly for subsequent procedures or T cells can then be separated from other non adherent mononuclear cells by a technique known as "rosetting". Negative selection of cells can also be used. Isolation of sub-populations of T cells can then be carried out with the aid of appropriate antibodies to cell surface antigens displayed on the surface of particular populations of T cells. Such techniques are sometimes referred to as positive or negative selection.

Once an appropriate T cell population or sub population has been isolated from a patient or animal, genetic or any other appropriate modification or manipulation may optionally be carried out before the resulting T cell population is expanded using the methods and supports of the invention. The manipulation may for example take the form of re-stimulation of the T cells with anti-CD3 and anti-CD28 antibodies to re-activate them.

Genetic or other manipulation of the T cells is an optional step and is not necessary for some therapies.

A yet further aspect of the invention provides a kit for expanding/activating CD4+CD25− T cells comprising a T cell receptor (TCR)/CD3 activator, a TCR co-stimulator activator and rapamycin. Preferably the activators are CD28 antibodies and CD3/TCR antibodies, which are preferably immobilized on a solid support.

The following examples are included to demonstrate preferred embodiments of the invention. It should be appreciated by those of skill in the art that the techniques disclosed in the examples which follow represent techniques discovered by the inventor(s) to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the scope of the invention.

EXAMPLES

Example 1

General Expansion Protocol for Generation of CD4+CD25+FOXP3− Regulatory T Cells

1) Isolate CD4+ T cells from peripheral blood or leukopheresis products by the use of Dynal® CD4 Positive isolation kit, Dynal® CD4 Negative Isolation kit, Dynabeads® MyPure™ CD4 T cell kit, or CD4 Microbeads MACS®.

2) Stimulate $1.5\times10^6$ CD4+ T cells with anti-CD3/CD28 Dynabeads (3:1 bead: T cell ratio) in X-vivo medium with 1000 U/ml IL-4 (optional), 20 U/ml IL-2 and 1 µM final concentration of Rapamycin. Total medium volume should be 1.5 ml per $1.5\times10^6$ CD4+ T cells in a 24 well plate. The protocol can be scaled up.

3) On day 2, add a 10× concentrate that contains 10,000 U/ml IL-4 (optional) and 10,000 U/ml IL-2. Add this in a volume that is 10% of the initial culture volume.

4) On day 4, add the cytokine concentrate similar to day 2.

5) On day 6, add the 10× cytokine concentrate again and take an aliquot to count the cells. This is the first time that the culture should be disturbed. Based on the count adjust the cell concentration to $1\times10^6$ CD4 cell/ml. Split wells and add culture medium containing Rapamycin, 1000 U/ml IL-4 (optional), 20 U/ml IL-2 to maintain cell concentration at $0.5\times10^6$ cells/ml.

6) From day 7 to day 12 count the cells daily. Split wells and add culture medium containing Rapamycin, 1000 U/ml IL-4 (optional), 20 U/ml IL-2 to maintain the cell concentration at $0.5\times10^6$ cells/ml. On day 12 the beads are removed using a magnet.

7) On day 14-15 the cells can be analyzed for surface marker expression and functional properties.

Example 2

Analysis of Properties of Expanded T Cells

CD4+ T cells were isolated from peripheral blood by negative and/or positive isolation as described in Example 1. After expansion with IL-2,+/−IL-4, CD3/CD28 Dynabeads®, with or without Rapamycin the expanded cells were analyzed for various surface markers (CD4, CD25, CD62L, CRTh2, CCR4, CXCR3, CCR7) and for intracellular FOXP3 expression and cytokine secretion. Suppressive capacity was analyzed in standard functional assays as described below.

The above mentioned surface markers are as follows:

CD62L: Lymph node homing adhesion molecule, expressed on naive T cells and naturally occurring CD4+ CD25+ Treg cells.

CRTh2: A marker expressed on all Th2 cells.

CCR4: Chemokine receptor expressed on Treg cells and Th2 cells.

CXCR3: Chemokine receptor expressed on inflammatory Th1 cells.

CCR7: Lymph node homing chemokine receptor expressed on naïve T cells, central memory T cells and naturally occurring CD4+CD25+ Treg cells.)

CD4+ T cells expanded without Rapamycin show low expression of CD25, CD62L and CCR7, and higher expression of CXCR3. The cytokine profile shows high levels of both Th1 and Th2 cytokines In contrast, the CD4+T cells expanded with Rapamycin have a phenotype of Treg cells with high CD25, low CXCR3 and low secretion of cytokines Approximately 70% of the expanded cells express high levels of CD25. None of the expanded T cells with or without Rapamycin have an increased expression of FOXP3. 10% of freshly isolated CD4+ T cells expressed FOXP3 and after expansion still only 10% of the cells expressed FOXP3.

Figure 1:
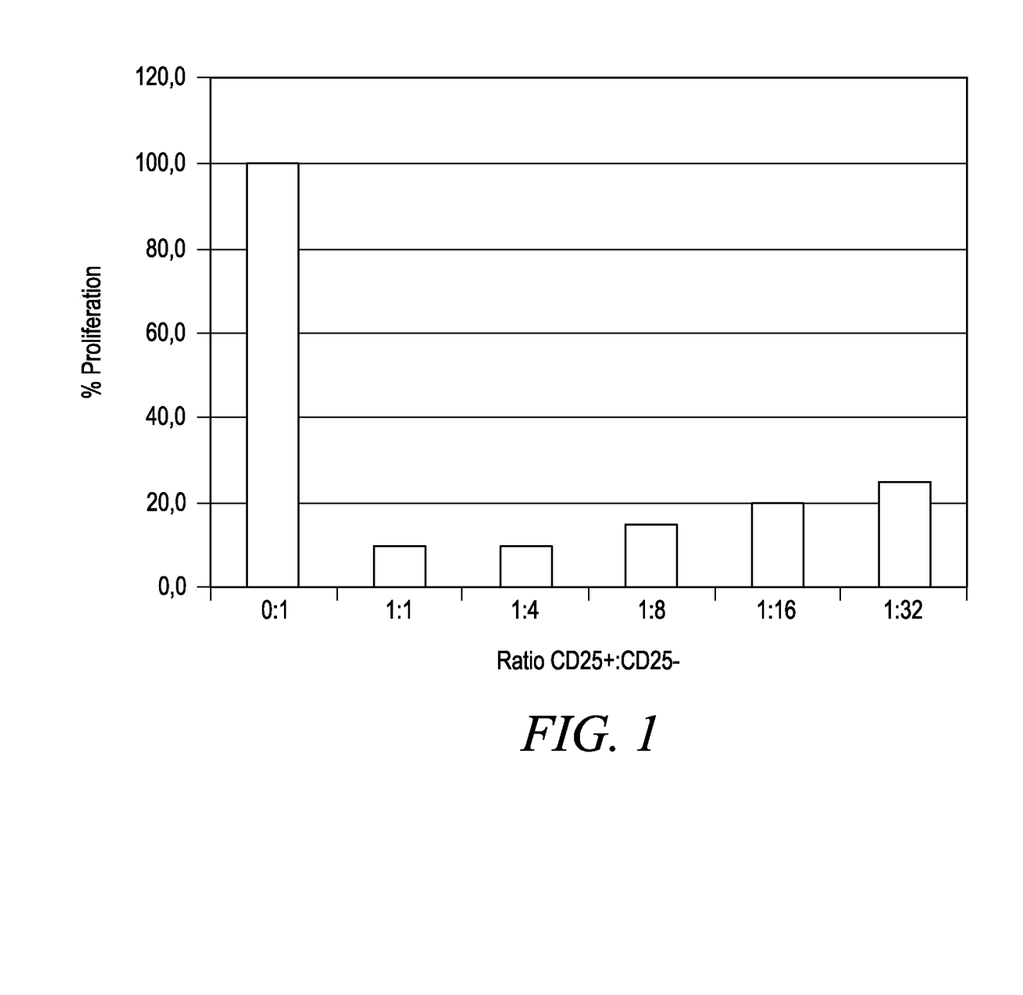
FIG. 1 shows the extent of proliferation of various ratios of T cells cultured with or without rapamycin in a standard proliferation assay. CD25− T cells (T cells cultured without Rapamycin) were analyzed for proliferative capacity in a standard proliferation assay using $^3$H Thymidine incorporation after 4 days stimulation. CD25+ T cells (T cells cultured with Rapamycin) were added to the CD25− T cells in a ratio from 1:1 to 1:32. The proliferative capacity of CD25− T cells alone was defined as 100% proliferation. The x-axis is the ratio of CD25+ cells to CD25− cells. The y-axis is percent proliferation.

Standard proliferation assays were performed using 75,000 CD25− T cells supplemented with CD25+ T cells to provide the ratios indicated in FIG. 1 and thymidine incorporation was analyzed after a period of 4 days. T cells expanded with Rapamycin (CD25+) were found to be capable of suppressing proliferation of non Rapamycin expanded T cells (CD25−). In the presence of CD25+ T cells, the CD25− T cells capacity to proliferate was inhibited by 90%. (FIG. 1).

Figure 2A:
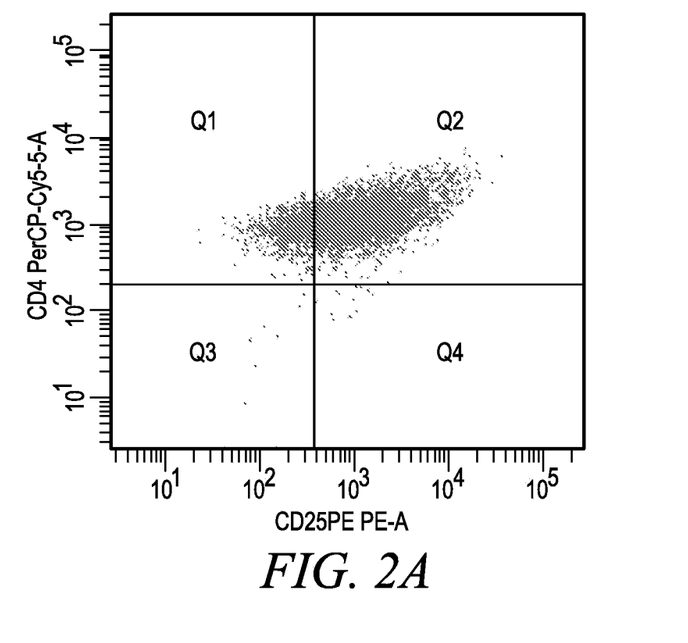
FIGS. 2A and 2B show flow cytometry analysis of CD4 and CD25 expression on CD4+T cells expanded (FIG. 2A) with rapamycin or (FIG. 2B) without rapamycin.
Figure 2B:
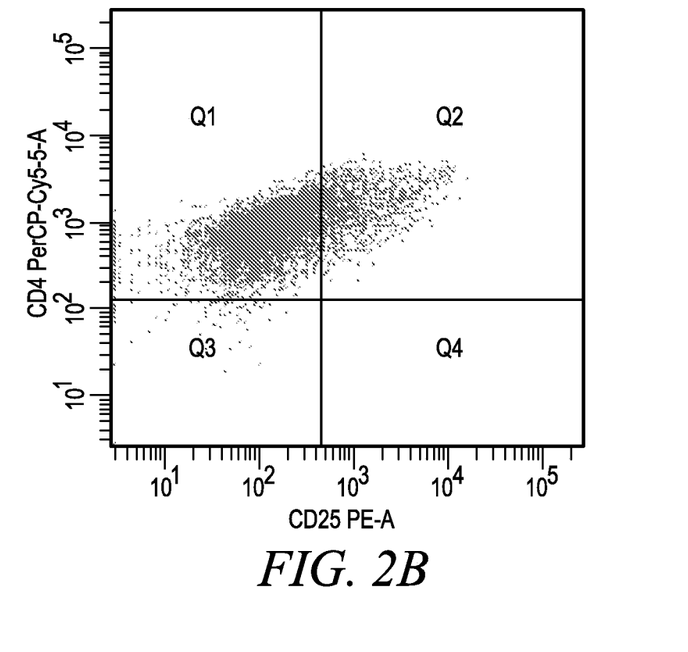

FIG. 2 illustrates the expression of CD4 and CD25 in CD4+ T cells expanded with or without rapamycin. Rapamycin expanded cells express 80% CD4+CD25+ T cells wherein in the absence of rapamycin only 20% of the T cells were CD4+ CD25+.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the scope and concept of the invention.

What is claimed is:

1. A method of generating immunosuppressive regulatory T cells from a sample containing a mixed population of CD4+ CD25+ and CD4+CD25− T cells, the method comprising:
    (a) preparing a mixture comprising:
        (i) the sample containing the mixed population of CD4+ CD25+ and CD4+CD25− T cells,
        (ii) an anti-CD3 antibody,
        (iii) an anti-CD28 antibody,
        (iv) interleukin 2, and
        (v) rapamycin; and (b) incubating the mixture prepared in (a) under conditions suitable for the selective expansion of CD4+CD25+FOXP3− T cells over other T cell subtypes,
wherein both the anti-CD3 antibody and the anti-CD28 antibody are immobilized on a solid phase, and
wherein interleukin 4 is not added to the mixture of (a).

2. The method of claim 1, wherein the anti-CD3 antibody and the anti-CD28 antibody are immobilized on the same solid phase.

3. The method of claim 1, wherein the anti-CD3 antibody and the anti-CD28 antibody are immobilized on different solid phases.

4. The method of claim 1, wherein the solid phase is a bead.

5. The method of claim 1, wherein the solid phase comprises glass, silica, latex, polymeric materials, plastic, tissue culture plastic, dextran, cellulose, polyethylene glycol, iron, or combinations thereof.

6. The method of claim 1, wherein the solid phase comprises magnetic beads, superparamagnetic beads, or magnetizable beads.

* * * * *